US007413902B2

(12) United States Patent
Bodnar et al.

(10) Patent No.: US 7,413,902 B2
(45) Date of Patent: *Aug. 19, 2008

(54) FEEDER-FREE CULTURE METHOD FOR EMBRYONIC STEM CELLS OR PRIMATE PRIMORDIAL STEM CELLS

(75) Inventors: Andrea G. Bodnar, Oshawa (CA); Choy-Pik Chiu, Cupertino, CA (US); Joseph D. Gold, San Francisco, CA (US); Margaret Inokuma, San Jose, CA (US); James T. Murai, San Bruno, CA (US); Michael D. West, Boston, MA (US)

(73) Assignee: Geron Corporation, Menlo Park, CA (US)

( * ) Notice: Subject to any disclaimer, the term of this patent is extended or adjusted under 35 U.S.C. 154(b) by 349 days.

This patent is subject to a terminal disclaimer.

(21) Appl. No.: 10/330,873

(22) Filed: Dec. 24, 2002

(65) Prior Publication Data

US 2003/0175956 A1   Sep. 18, 2003

Related U.S. Application Data

(60) Division of application No. 09/530,346, filed as application No. PCT/US98/22619 on Oct. 23, 1998, now Pat. No. 6,800,480, which is a continuation-in-part of application No. 08/956,684, filed on Oct. 23, 1997, now abandoned, which is a continuation-in-part of application No. 08/961,628, filed on Oct. 31, 1997, now abandoned, which is a continuation-in-part of application No. 08/961,629, filed on Oct. 31, 1997, now abandoned, which is a continuation-in-part of application No. 08/990,560, filed on Dec. 15, 1997, now abandoned.

(51) Int. Cl.
    *C12N 5/02* (2006.01)
(52) U.S. Cl. .................................... 435/377; 435/375
(58) Field of Classification Search .............. 435/366, 435/377
    See application file for complete search history.

(56) References Cited

U.S. PATENT DOCUMENTS

| 5,166,065 A | 11/1992 | Williams et al. ......... 435/240.1 |
| 5,332,672 A | 7/1994 | Conover et al. ......... 435/240.2 |
| 5,405,772 A | 4/1995 | Ponting ................ 435/240.31 |
| 5,453,357 A | 9/1995 | Hogan ..................... 435/7.21 |
| 5,523,226 A | 6/1996 | Wheeler ................. 435/240.2 |
| 5,583,016 A | 12/1996 | Villeponteau et al. ...... 435/91.3 |
| 5,639,618 A | 6/1997 | Gay ......................... 435/7.21 |
| 5,690,926 A | 11/1997 | Hogan ..................... 424/93.1 |
| 5,843,780 A | 12/1998 | Thomson ................... 435/363 |
| 5,914,268 A | 6/1999 | Keller et al. ............... 435/325 |
| 5,922,597 A | 7/1999 | Verfaillie et al. ......... 435/372.1 |
| 5,942,435 A | 8/1999 | Wheeler ..................... 435/325 |
| 6,200,806 B1 | 3/2001 | Thomson ................... 435/366 |
| 6,245,566 B1 | 6/2001 | Gearhart et al. ............ 435/384 |
| 6,642,048 B2 * | 11/2003 | Xu et al. .................... 435/366 |
| 6,800,480 B1 * | 10/2004 | Bodnar et al. .............. 435/325 |
| 2003/0113910 A1 | 6/2003 | Levanduski | |

FOREIGN PATENT DOCUMENTS

| AU | 199912771 B2 | 5/1999 |
| CA | 2190528 A1 | 7/1996 |
| CA | 2285274 A1 | 10/1998 |
| EP | 0695 351 B1 | 12/1999 |
| FR | 2744133 | 8/1997 |
| WO | WO 94/26884 A1 | 11/1994 |
| WO | WO 95/00632 A1 | 1/1995 |
| WO | WO 96/17627 | 6/1996 |
| WO | WO 96/22362 A1 | 7/1996 |
| WO | WO 97/21802 A1 | 6/1997 |
| WO | WO 97/28253 | 8/1997 |
| WO | WO 97/30151 | 8/1997 |
| WO | WO 98/30679 | 7/1998 |
| WO | WO 98/43679 | 10/1998 |
| WO | WO 99/42122 | 8/1999 |

(Continued)

OTHER PUBLICATIONS

Lim et al. Proteosome Analysis of Conditioned Medium from Mouse Embryonic Fibroblast Feeder Layers which Support the Growth of Human Embryonic Stem Cells. Proteomics. 2002, vol. 2, pp. 1187-1203.*

(Continued)

*Primary Examiner*—Deborah Crouch
(74) *Attorney, Agent, or Firm*—E. Stewart Mittler

(57) ABSTRACT

Methods and materials for culturing primate-derived primordial stem cells are described. In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from feeder cells and an extracellular matrix component derived from feeder cells. The medium further includes non-essential amino acids, an anti-oxidant, and a first growth factor selected from nucleosides and a pyruvate salt.

5 Claims, No Drawings

FOREIGN PATENT DOCUMENTS

WO        WO 01/00650 A1     1/2001
WO        WO 01/51616 A2     7/2001

OTHER PUBLICATIONS

Pera et al. Human Embryonic Stem Cells. Journal of Cell Sci. 2000, vol. 113, pp. 5-10.*
Eiges et al. A Molecular View on Pluripotent Stem Cells. FEBS Letters. 2002, vol. 529, pp. 135-141.*
Gretch-Nir et al. Vascular Gene Expression and Phenotypic Correlation During Differentiation of Human Embryonic Stem Cells. Developmental Dynamics. 2005, vol. 232, pp. 487-497.*
Baribault, H., et al., "Embryonic Stem Cell Culture and Gene Targeting in Transgenic Mice", Mol. Biol. Med. 6:481-492 (1989).
Berger, C., et al., "Self Renewal of Embryonic Stem Cells in the Absence of Feeder Cells and Exogenous Leukaemia Inhibitory Factor", Growth Factors, 14:145-159 (1997).
Bongso, A., et al., "Improved Quality of Human Embryos When Co-Cultured with Human Ampullary Cells", Hum Reprod., 4:706-713 (1989).
Bradley, A., et al., "Modifying the Mouse: Design and Desire", Biotechnology, 10:534-539 (1992).
Evans, M., et al., "Establishment in Culture of Pluripotential Cell from Mouse Embryos", Nature, 292:154-156 (1981).
Gardner, D., et al., "Culture and Transfer of Human Blostocysts Increases Implantation Rates and Reduces the Need for Multiple Embryo Transfers", Fertil. Steril, 69:84-88 (1998).
Gendall, A., et al., "Isolation and Characterization of a Leukemia Inhibitory Factor-Independent Embryonic Stem Cell Line", Int. J. Biochem Cell Biol., 29(5):829-840 (1997).
Gendron, R., et al., "Induction of Embryonic Vasculogenesis by bFGF and LIF in Vitro and in Vivo", Developmental Biology, 177:332-346 (1996).
GibcoBrl Life Technologies Catalogue and Ref. Guide, pp. 1-2 through 1-4, 1-94 and 1-95 (1993).
Keller, G., "In Vitro Differentiation of Embryonic Stem Cells", Cell Biology, 7:862-869 (1995).
Koshimizu, U., et al., "Functional Requirement of gp130-mediated Signaling for Growth and Survival of Mouse Primordial Germ Cells In Vitro and Derivation of Embryonic Germ (EG) Cells", Development, 122:1235-1242 (1996).
Koshimizu, U., et al., "Rapid Communication Retinoic Acid Is a Potent Growth Activator of Mouse Primordial Germ Cells in Vitro", Developmental Biology, 168:683-685 (1995).
Matsui, Y., et al., "Derivation of Pluripotential Embryonic Stem Cells from Murine Primordial Germ Cells in Culture", Cell, 70:841-847 (1992).
Nichols, J., et al., "Establishment of Germ-line-Competent Embryonic Stem (ES) Cells Using Differentiation Inhibiting Activity", Development, 110:1341-1348 (1990).
Nichols, J., et al., "Derivation of Germline Competent Embryonic Stem Cells with a Combination of Interleukin-6 and Soluble Interleukin-6 Receptor", Experimental Cell Research, 215:237-239 (1994).
Pease, S., et al., "Isolation of Embryonic Stem (ES) Cells in Media Supplemented with Recombinant Leukemia Inhibitory Factor (LIF)", Developmental Biology, 141:344-352 (1990).
Pedersen, R., "Studies of In Vitro Differentiation with Embryonic Stem Cells", Reprod. Fertil. Dev., 6:543-52 (1994).
Robertson, E., "Derivation and Maintenance of Embryonic Stem Cell Cultures", Methods in Mol. Bio., 75:173-184 (1997).
Rose, T., et al., "Oncostatin M (OSM) Inhibits the Differentiation of Pluripotent Embryonic Stem Cells In Vitro", Cytokine, 6(1):48-54 (1994).
Shamblott, M., et al., "Derivation of Pluripotent Stem Cells from Cultured Human Primordial Germ Cells", Proc. Natl. Acad. Sci. USA, 95:13726-13731 (1998).
Smith, A., et al., "Inhibition of Pluripotential Embryonic Stem Cell Differentiation by Purified Polypeptides", Nature, 336:668-690 (1998).
Thomson, J., et al., "Embryonic Stem Cell Lines Derived from Human Blastocysts", Science, 282:145-47 (1998).
Thomson, J., et al., "Isolation of a Primate Embryonic Stem Cell Line", Proc. Natl. Acad. Sci. USA, 92:7844-7848 (1995).
Thomson, J., et al., "Primate Embryonic Stem Cells", Current Topics in Developmental Biology, 38:133-165 (1998).
Worrall, D., et al., "A Carrot Leucine-Rich-Repeat Protein That Inhibits Ice Recrystallization", Science, 282:115-117 (1998).
Williams, R., et al., "Myeloid Leukaemia Inhibitory Factor Maintains the Developmental Potential of Embryonic Stem Cells", Nature, 336:684-687 (1988).
Baribault, H., et al., "Embryonic Stem Cell Culture and Gene Targeting in Transgenic Mice", Mol. Biol. Med., 6:481-492 (1989).
Keller, G., "In Vitro Differentiation of Embryonic Stem Cells", Current Opinion in Cell Biology, 7:862-869 (1995).
Koshimizu, U., et al., "Rapid Communication: Retinoic Acid is a Potent Growth Activator of Mouse Primordial Germ Cells in Vitro", Developmental Biology, 168:683-685 (1995).
Nichols, J., et al., "Establishment of Germ-line-competent Embryonic Stem (ES) Cells Using Differentiation Inhibiting Activity", Development, 110:1341-1348 (1990).
Nichols, J., et al., "Derivation of Germline Competent Embryonic Stem Cells with a Combination of Interleukin-6 and Soluble Interleukin-6 Receptor", Experimental Cell Res., 215:237-239 (1994).
Wenk, J., et al., "Glycolipids of Germ Cell Tumors: Extended Globo-Series Glycolipids are a Hallmark of Human Embryonal Carcinoma Cells", Int. J. Cancer, 58:108-115 (1994).
Xu, C., et al., "Feeder-free growth of undifferentiated human embryonic stem cells," Nat Biotechnol 19:971 (2001).
Lebkowski, et al., Human embryonic stem cells: Culture, differentiation, and genetic modification for regenerative medicine applications, Cancer J. Suppl 2:S83-93 (2001).
Martin, Isolation of a pluripotent cell line from early mouse embryos cultured in medium conditioned by teratocarcinoma stem cells, Proc Natl Acad Sci USA 78:7634 (1981).
Smith, et al., Medium conditioned by feeder cells inhibits the differentiation of embryonal carcinoma cultures, Exp Cell Res 145:458 (1983).
Andrews, P. et al., "Inhibition of proliferation and induction of differentiation of pluripotent human embryonal carcinoma cells by osteogenic protein-1 (or bone morphogenetic protein-7)," Lab. Invest. 71(2):243-51 (1994).
Bongso, A. et al., "Isolation and culture of inner cell mass cells from human blastocysts," Hum. Reprod. 9(11):2110-7 (1994).
Cibelli, J. et al., "Parthenogenic stem cells in nonhuman primates," Science 295:819 (2002).
Gearhart, J., "New Potential for Human Embryonic Stem Cells," Science 282:1061-2 (1998).
Wells, D. & Delhanty, J., "Preimplantation genetic diagnosis: applications for molecular medicine," Trends Molec. Med. 7(1):23-30 (2001).

* cited by examiner

SEQUENCE LISTING

```
<160> NUMBER OF SEQ ID NOS: 2

<210> SEQ ID NO 1
<211> LENGTH: 30
<212> TYPE: DNA
<213> ORGANISM: Homo sapiens

<400> SEQUENCE: 1
gcgcggctta cccttaccct tacccctaacc                                    30

<210> SEQ ID NO 2
<211> LENGTH: 18
<212> TYPE: DNA
<213> ORGANISM: Homo sapiens

<400> SEQUENCE: 2
aatccgtcga gcagagtt                                                  18
```

FEEDER-FREE CULTURE METHOD FOR EMBRYONIC STEM CELLS OR PRIMATE PRIMORDIAL STEM CELLS

REFERENCE TO RELATED APPLICATIONS

This application is a divisional of U.S. patent application Ser. No. 09/530,346 filed Aug. 29, 2000 now U.S. Pat. No. 6,800,480, pending, which is hereby incorporated herein by reference in its entirety. The Ser. No. 09/530,346 application is the 35 USC § 371 National Stage of International Application PCT/US98/22619 designating the U.S. (filed Oct. 23, 1998, and published on Apr. 29, 1999 as WO 99/20741); which is a continuation-in-part of U.S. patent application Ser. Nos. 08/956,684 (filed Oct. 23, 1997), 08/961,628 (filed Oct. 31, 1997), 08/961,629 (filed Oct. 31, 1997), and 08/990,560 (filed Dec. 15, 1997), all four of which have since been abandoned.

1 BACKGROUND OF THE INVENTION 1.1 Field of the Invention

This invention relates to the field of stem cell culture media and to methods for culturing such cells. More particularly, the present invention provides methods and materials for culturing primate-derived primordial stem cells in a substantially undifferentiated state with and without a feeder layer. The present invention has applications in the areas of cell culture, tissue transplantation, drug discovery, and gene therapy.

1.2 The Related Art

Stem cells are cells capable of differentiation into other cell types having a particular, specialized function ("fully differentiated" cells) or other types of stem cells which are capable of differentiation into a more narrow range of cell types ("pluripotent" cells). Stem cells having the ability to differentiate into any type of cell, i.e., pluripotent or fully differentiated, are called "totipotent". Such cells are also referred to as "primordial stem cells". There has been great interest in isolating and growing primordial stem cells from primates, especially from humans, as such primordial stem cells could provide a supply of readily available cells and tissues of all types for use in transplantation, drug discovery, and gene therapy in humans. Methods for isolating and growing primordial stem cells from primates have been described. Procedures for isolating and growing human primordial stem cells are described in co-pending U.S. patent application Ser. No. 08/829,372. Procedures for obtaining Rhesus monkey and other non-human primate primordial stem cells are described in co-pending U.S. patent applications Ser. Nos. 08/376,327; 08/591,246; 08/665,217; and WO 96/22362. Each of these patent applications is incorporated herein by reference in its entirety and for all purposes. In addition, methods for isolating Rhesus monkey primordial stem cells are described in Thomson et al. (1995 Proc. Natl. Acad. Sci. USA 92:7844-7848) also incorporated herein by reference in its entirety and for all purposes.

Unfortunately, current methods for growing primordial stem cells derived from primates in culture have not been as clearly defined as, and are relatively inefficient compared with, methods for culturing primordial stem cells for other species such as mouse. For example, current methods of culturing primate-derived primordial stem cells require a feeder layer that complicates and slows the process of cell cultivation. In addition, the formulation of an optimal culture media for propagating undifferentiated totipotent primate-derived primordial stem cells remains to be determined.

In particular, it is desirable to maintain cultures of totipotent primordial stem cells for extended periods or indefinitely. The ability to maintain cultures of undifferentiated, totipotent, primate-derived primordial stem cells for long periods facilitates the use of such cells for therapeutic purposes. Moreover, it would be desirable to grow cultures of substantially undifferentiated primate-derived primordial stem cells for periods sufficient to allow the production of primate-derived primordial stem cells having multiple genetic modifications for the production of tissues and for gene therapy.

2 SUMMARY OF THE INVENTION

The present invention provides methods and reagents for culturing primate-derived primordial stem cells in a substantially undifferentiated state. The methods and materials described herein provide improved culturing conditions that allow the preparation of primate-derived primordial stem cells having single or multiple genetic modifications. Such modified cells have important applications in gene therapy and tissue transplantation/implantation therapies.

In one aspect, the present invention provides a cell culture medium for growing primate-derived primordial stem cells in a substantially undifferentiated state. In one embodiment, the cell culture medium of the invention comprises a low osmotic pressure, low endotoxin basic medium that is effective to support the growth of primate-derived primordial stem cells. This basic medium is combined with a nutrient serum effective to support the growth of primate-derived primordial stem cells and a substrate selected from the group of feeder cells, such as mouse embryo fibroblast cells and STO cells, and an extracellular matrix derived from the feeder cells. The medium further includes non-essential amino acids, an antioxidant (for example, β-mercaptoethanol), and, optionally, a first growth factor selected from the group consisting of nucleosides and a pyruvate salt.

In more specific embodiments, the basic medium of the cell culture medium has an osmotic pressure of less than about 300 mOsm/kg. Still more specific embodiments are those for which the basic medium has an osmotic pressure of about 280 mOsm/kg. Yet other embodiments of the cell culture medium of the present invention include those for which the basic medium has an endotoxicity of less than about 0.1 endotoxin units per ml. More specific embodiments for which the endotoxicity of the basic medium is less than about 0.1 endotoxin units per ml are those embodiments for which the endotoxicity of the base medium is about 0.03 endotoxin units per ml.

In other embodiments the cell culture medium of the invention further includes a second growth factor. In a preferred embodiment, the second growth factor is selected from the group consisting of: Anti-L-8, Anti-TGF-β5, Anti-BDNF, Anti-TNF-β, Anti-VEGF, Anti-TGF-β, IL-11, IL-6, IL-6+ soluble IL-6 receptor, IL-1α, IL-1β, LIF, Anti-HB-EGF, IL-17, TFG-β-1 LAP, MCP-1, bFGF, FGF-4, PDGF Soluble Receptor A, dexamethasone and Forskolin.

Suitable growth factors for use in the present invention can be determined using a method for screening for growth factors that is provided in another aspect of the present invention. According to one embodiment of this aspect of the invention, primate-derived primordial stem cells are grown using a cell culture medium of the present invention in the presence of a putative growth factor. A determination is made as to whether the putative growth factor enhances the growth of undifferentiated primate-derived primordial stem cells. Substances that enhance the growth of primate-derived primordial stem cells are classified as growth factors.

In another aspect, the present invention provides a culture of primate primordial cells, comprising at least one primate-derived primordial stem cell in fluid contact with the cell culture medium of the invention. Such cells can be human- or Rhesus-derived primordial stem cells, for example.

In still another aspect, the present invention provides methods for producing primate cell lines having one or more genetic modifications. According to one embodiment of this aspect of the present invention, primordial stem cells are grown using a cell culture medium of the invention. A first gene or nucleic acid is introduced into, or a first gene is modified in, these cells and a first clone population is derived. In a further embodiment, a second gene or nucleic acid is introduced into, or a second gene is modified in, the cells of the first clone population and a second clone population is derived. In some embodiments, the primordial stem cells are derived from human embryonic cells. In other embodiments the primordial stem cells are PSC43 cells, an aneuploid variant of Rhesus embryonic stem cells that is capable of growing in a feeder-free cell culture as described hereinbelow. This cell line has been found effective for screening for growth factors for cell culture media.

These and other aspects and advantages will become apparent when the Description below is read in conjunction with the accompanying Examples.

3 DESCRIPTION OF SOME EMBODIMENTS OF THE INVENTION

The present invention provides methods and materials for culturing primate-derived primordial stem cells in a substantially undifferentiated state and for identifying and quantifying undifferentiated primate-derived primordial stem cells. In addition, the present invention also provides screens for discovering substances that accelerate or retard the differentiation of such cells. In addition to the many benefits deriving from access to primate-derived primordial stem cells, the methods and materials provided by the present invention can be applied to produce primordial stem cells having single or multiple genetic modifications. Primate-derived primordial stem cells having such serial modifications have important applications, especially with respect to applications where euploid primate cells having genetic modifications are useful or required. Examples of such applications include, but are not limited to, the development of cell-based models for primate, especially human, diseases, as well as the development of specialized tissues for transplantation to treat genetic diseases.

3.1 Definitions

The following terms will be defined as provided in this Section 3.1 unless otherwise stated. All other terminology used herein will be defined with respect to its usage in the particular art to which it pertains unless otherwise noted.

3.1.1 Basic Medium

Basic Medium refers to a solution of salts and nutrients that is effective to support the growth of primate-derived primordial stem cells in culture.

3.1.2 Conditioned Medium

Conditioned Medium refers to a growth medium that is further supplemented with soluble factors derived from feeder cells.

3.1.3 Embryonic Germ Cells

Embryonic Germ Cells or EG Cells are cells derived from the primordial germ cells of an embryo or fetus that are destined to give rise to sperm or eggs.

3.1.4 Embryonic Stem Cells

Embryonic Stem Cells or ES Cells are cells obtained from morula or blastocyst stages of a pre-implantation stage embryo.

3.1.5 Extracellular Matrix

Extracellular Matrix or Defined Matrix as used for the purposes of describing the present invention refers to one or more substances that provide substantially the same conditions for supporting cell growth as provided by the surfaces of feeder cells.

3.1.6 Feeder Cells

Feeder Cells as used for the purposes of describing the present invention refers to non-primordial stem cells on which primate-derived primordial stem cells are plated, which non-primordial stem cells provide a milieu conducive to the growth of the plated primate-derived primordial stem cells.

3.1.7 Growth Factor

Growth Factor as used for the purposes of describing the present invention refers to a substance that is effective to promote the growth of primordial stem cells that is not otherwise a component of the conditioned medium. Such substances include, but are not limited to, cytokines, chemokines, small molecules, neutralizing antibodies, and proteins.

3.1.8 Low Osmotic Pressure Medium

Low Osmotic Pressure Medium refers to a solution having an osmotic pressure of less than about 300 milli-osmols per kilogram ("mOsm/kg").

3.1.9 Non-essential Amino Acids

Non-essential Amino Acids refers to the amino acids L-alanine, L-asparagine, L-aspartic acid, L-glutamic acid, glycine, L-proline, and L-serine.

3.1.10 Primordial Stem Cell

Primordial Stem Cell refers to either an embryonic stem cell or an embryonic germ cell as defined herein.

3.1.11 Primate-Derived Primordial Stem Cell

Primate-Derived Primordial Stem Cell refers to a primordial stem cell that is obtained from a primate species, including humans and monkeys, including genetically modified primordial stem cells obtained from a primate.

3.1.12 Pluripotent

Pluripotent refers to cells that are capable of differentiating into one of a plurality of different cell types although not necessarily all cell types. One example of pluripotent cells are bone marrow stem cells which are capable of differentiating into various blood cell types such as lymphocytes and red blood cells but not nerve cells. Thus, it will be recognized that while all totipotent cells are pluripotent, not all pluripotent cells are totipotent.

3.1.13 Substantially Undifferentiated

Substantially Undifferentiated refers to a group of primate-derived primordial stem cells of which at least about 50% are in an undifferentiated, totipotent, state.

3.1.14 Totipotent

Totipotent refers to cells that are capable of differentiating into any cell type including pluripotent and fully differentiated cells (i.e., cells no longer capable of differentiation into various cell types), such as, without limitation, bone marrow stem cells, cardiac muscle cells, astrocytes, or connective tissue cells.

3.2 Growing and Maintaining Primate-Derived Primordial Stems Cells in a Substantially Undifferentiated State As described in Sections 3.2.1 and 3.2.2 below, the present invention provides cell culture media, growth factors, and methods for growing and maintaining cultures of primate-derived primordial stem cells in a substantially undifferentiated state that provides for the growth and maintenance of totipotent primate-derived primordial stem cells for periods longer than heretofore available. The improved cell culture media of the invention can also be used to screen for additional growth factors and useful combinations of growth factors as described in Section 3.3 below. As discussed in Section 3.4 below, the ability to grow primate-derived primordial stem cells in a substantially undifferentiated, totipotent state using the improved cell culture media, growth factors, and methods provided herein provides important benefits including the ability to produce primate-derived primordial cell lines having single or multiple genetic modifications having important therapeutic applications.

3.2.1 Cell Culture Media for Growing and Maintaining Primate-Derived Primordial Stem Cells in a Substantially Undifferentiated State In one aspect, the present invention provides improved cell culture media for growing and maintaining primate-derived primordial stem cells in a substantially undifferentiated state. In one embodiment, the cell culture media of the present invention includes a low osmotic pressure, low endotoxin basic medium that is effective to support growth of primate-derived primordial stem cells; a nutrient serum effective to support growth of primate-derived primordial stem cells; a substrate selected from the group consisting of feeder cells, such as mouse (or other species) embryo fibroblast cells and STO cells, and an extracellular matrix derived from such feeder cells; non-essential amino acids; an anti-oxidant (reducing agent); and a first growth factor selected from the group consisting of nucleosides and a pyruvate salt.

In one particular embodiment, the osmotic pressure of the basic medium is less than about 300 milli-osmols per kilogram ("mOsm/kg"), and, more particularly, less than about 280 mOsm/kg. In one embodiment, the osmotic pressure of the basic medium is about 280 mOsm/kg. The endotoxicity, as measured in endotoxin units per milliliter ("eu/ml") is less than about 0.1 eu, and, in a more particular embodiment, less than about 0.05 eu/ml. In a still more particular embodiment, the endotoxicity of the basic medium is less than about 0.03 eu/ml. In one particular embodiment, the endotoxicity of the basic medium is about 0.03 eu/ml. Methods for measuring endotoxicity are known in the art. For example, a preferred method is described in the "Guideline on Validation of the Limulus Amebocyte Lysate Test as an End-product Endotoxin Test for Human and Animal Parental Drugs, Biological Products and Medical Devices" published by the U.S. Department of Health and Human Services, FDA, December 1987.

The nutrient serum can be any serum or serum-based solution that supplies nutrients effective to maintain the growth and viability of primate-derived primordial stem cells. Examples of such serum include, without limitation, fetal bovine serum ("FBS") and fetal calf serum ("FCS"). In one embodiment, the serum is FBS. In a more particular embodiment, the FBS is provided in a concentration of between about 25% and about 1%. In a more particular embodiment, the FBS is provided in a concentration of between about 20% and about 2.5%. In as still more particular embodiment, the concentration of FBS in the cell culture medium is 20%. In another embodiment, the concentration of FBS is 2.5%.

Other embodiments of the cell culture media of the present invention include those for which a first growth factor includes one or more nucleosides. In more specific embodiments, the nucleoside(s) are selected from the group consisting of adenosine, cytosine, guanine, uridine and thymidine. Still more particular embodiments include those for which the nucleoside(s) selected are in about equal concentrations. More specific embodiments include those for which the concentration of nucleoside(s) included in the cell culture media of the invention is between about 0.1 µM and about 30 µM, and, more particularly, the media concentration is between about 0.3 µM and about 10.0 µM. In a still more particular embodiment, the concentration of nucleoside(s) is between about 0.5 µM and about 5.0 µM. In one embodiment, the concentration of nucleoside(s) is about 0.1 µM. In still other embodiments, the first growth factor can be a pyruvate salt, such as sodium pyruvate or another pyruvate salt that is effective to maintain and/or enhance cell growth in a substantially undifferentiated state such as, for example, potassium pyruvate. The pyruvate salt can be combined with one or more of the above-described nucleosides. In one embodiment, the pyruvate salt is provided in a concentration of 1 mM.

In some embodiments a second growth factor (as defined in Section 3.1.7) is also provided, again, to assist in the maintenance of cultures of primate-derived primordial stem cells in a substantially undifferentiated state. The identities and effective concentrations of such second growth factors can be determined using the methods described in Section 3.3 below or using techniques known to those of skill in the art of culturing cells. In one embodiment, a second growth factor is included with the cell culture media of the invention which second growth factor is selected from the group consisting of: Anti-IL-8, Anti-TGF-β5, Anti-BDNF, Anti-TNF-β, Anti-VEGF, Anti-TGF-β, IL-11, IL-6, IL-6+soluble IL-6 receptor, IL-1α, IL-1β, LIF, Anti-HB-EGF, IL-17, TFG-β-1 LAP, MCP-1, bFGF, FGF-4, PDGF Soluble Receptor A, glucocorticoid (e.g., dexamethasone) and Forskolin. The second growth factor can be one or more of the above-listed substances as well as other growth factors that can be easily identified.

In one embodiment, the second growth factor is forskolin ([3R-(3α, 4αβ, 5β, 6β, 6αα, 10α, 10αβ, 10bα)]-5-(acetyloxy)-3-ethenyldodecahydro-6, 10, 10b-trihydroxy-3, 4a, 7, 7, 10a-pentamethyl-1H-naphtho[2, 1-b]pyran-1-one). In one embodiment, the forskolin is added to the cell culture medium of the invention to achieve a concentration of less than about 30 µM. In a more particular embodiment the concentration of forskolin in the cell culture medium of the invention is between about 5 µM and about 15 µM, and, more particularly, between about 8 µM and about 12 µM. In one embodiment, the concentration of forskolin added to the cell culture medium of the invention is about 10 µM. In another embodiment, the concentration of forskolin is about 20 µM.

In another embodiment, the second growth factor is selected from the group consisting of "basic" FGF ("bFGF") and/or FGF-4, alone or in combination with human insulin, anti-TGF-β-1 antibody, and EGF. In one embodiment, the concentration of bFGF in the cell culture medium is about 5 nanograms/milliliter ("ng/ml"), either alone or combined with human insulin. When combined with bFGF, the concentration of human insulin is about 8 µg/ml. In those embodiments for which EGF is added to the cell culture medium of the invention, the concentration of EGF is about 0.1 ng/ml.

The cell culture media of the invention also includes an anti-oxidant (reducing agent), such as β-mercaptoethanol. In a preferred embodiment, the β-mercaptoethanol has a concentration of about 0.1 mM. Other anti-oxidants such as monothioglycerol or dithiothreitol ("DTT"), alone or in combination, can be used to similar effect. Still other equivalent substances will be familiar to those of skill in the cell culturing arts.

In addition to the above-described components, the cell culture media of the invention further includes a substrate selected from the group consisting of feeder cells, such as mouse (or other species) embryo fibroblast cells and STO cells, and an extracellular matrix derived from such feeder. In one embodiment, mouse embryo fibroblasts obtained from dissection of 13.5-day-old CF-1 strain mice are used. Other suitable feeder cell lines will be familiar to those of skill in the cell culture art. If feeder cells are used, as opposed to extracellular matrix, the cells can be mitotically inactivated (e.g., by irradiation or chemically to prevent further growth and seeded on plates. The primate-derived primordial stem cells can then be grown on the plate in addition to the feeder cells. Alternatively, the feeder cells can be first grown to confluence and then inactivated to prevent further growth. It will be appreciated that such an approach has the advantage of simplifying the management of the cell culture as the growth of only one set of cells, the primordial stem cells, need only be monitored.

Not wishing to be bound to any theory, it is believed that the use of such feeder cells, or an extracellular matrix derived from such feeder cells, provides one or more substances necessary to promote the growth of primate-derived primordial stem cells and/or prevent or decrease the rate of differentiation of such cells. Such substances are believed to include membrane-bound and/or soluble cell products that are secreted into the surrounding medium by the cells. Thus, those of skill in the cell culturing arts will recognize that additional cell lines can be used with the cell culture medium of the present invention to equivalent effect and that such additional cell lines can be identified using standard methods and materials. In addition, those of skill will also recognize that one or more substances produced by the feeder cells, or contained in the extracellular matrix, can be identified and added to the cell culture medium of the invention to obviate the need for such feeder cells and/or such extracellular matrix.

In one particular embodiment of the invention, the preparation of which is described in detail in Section 4.1 below, a cell culture medium provided by the present invention includes the components and concentrations set forth in Table 1

TABLE 1

| Medium Component | Identity, Amount, and Supplier |
|---|---|
| Basic Medium | 280 mOsm/kg Dulbecco's Modified Eagle Medium (DMEM, 4500 mg glucose per liter, with L-glutamine (GIBCO)) |
| Nutrient Serum | 20% fetal bovine serum (HyClone) |
| Substrate | Mouse embryo fibroblasts obtained from 13.5-day-old embryos of CF-1 strain mice |
| Non-essential Amino Acids | 0.1 mM non-essential amino acid stock solution (GIBCO)† |
| β-mercaptoethanol | 0.1 mM β-mercaptoethanol (Sigma) |
| First Growth Factor | a final medium concentration of 1 μM each of adenosine, guanosine, thymidine, cytidine, and uridine (Sigma) and 1 mM sodium pyruvate (Sigma) |

†This solution includes L-alanine (8.9 mg/l), L-asparagine monohydrate (15 mg/l), L-aspartic acid (13.3 mg/l), L-glutamic acid (14.7 mg/l), glycine (7.5 mg/l), L-proline (11.5 mg/l), and L-serine (10.5. mg/l).

3.2.2 Growing Primate-Derived Primordial Stem Cells Using the Cell Culture Media of the Invention In another aspect, the present invention provides methods for growing primate-derived primordial stem cells in a substantially undifferentiated state and cultures of such cells in such cell culture media described above in Section 3.2.2. Detailed examples of the methods provided by the present invention can be found in Sections 4.1 and 4.2 below.

The primate-derived primordial stem cells to be cultured can be obtained using known methods and materials. Procedures for isolating human primordial stem cells are described in co-pending U.S. patent application Ser. No. 08/829,372, filed on Mar. 31, 1997. Procedures for obtaining Rhesus monkey and other non-human primate primordial stem cells are described in co-pending U.S. patent application Ser. Nos. 08/376,327, filed Jan. 20, 1995; 08/591,246, filed Jan. 18, 1996; WO 96/22362, published Jul. 25, 1996; 08/665,217, filed Jun. 14, 1996; and 08/874,695, filed Jun. 13, 1997. Each of these patent applications is incorporated herein by reference in their entirety and for all purposes. In addition, methods for isolating Rhesus monkey primordial stem cells can be found in Thomson et al. (1995 Proc. Natl. Acad. Sci. USA 92:7844-7848) also incorporated herein by reference in its entirety and for all purposes.

Once isolated, the primate-derived primordial stem cells are cultured using the above-described conditioned medium using any of a variety of techniques. In one embodiment, a container holds feeder cells in a non-conditioned medium. A matrix of lysed feeder cells is prepared using standard methods. One example of the preparation of such a matrix is provided in Section 4.2 below. The primordial stem cells to be cultured are then added atop the matrix along with the conditioned medium. Alternatively, the primate-derived primordial stem cells can be grown on living feeder cells using methods known in the cell culture arts. The growth of the primordial stem cells is then monitored to determine the degree to which the cultured cells have become differentiated. In one embodiment, described in Section 4.2 below, a marker for alkaline phosphatase is used to ascertain which cells have differentiated. When a sufficient number of cells have differentiated, or when the culture has grown to confluence, at least a portion of the undifferentiated cells is passaged. The determination to passage the cells and the techniques for accomplishing such passaging can be performed using standard techniques.

3.3 Screens for Growth Factors

In another aspect, the present invention provides screens for determining growth factors that promote or inhibit the differentiation of primate-derived primordial stem cells in culture. In one embodiment, an aneuploid variant of Rhesus 278.5 ES cells having 43 chromosomes, hereinafter referred to as "PSC43 cells", is used as a primary screen to identify substances that promote the growth of primate-derived primordial stem cells in a substantially undifferentiated state. In one embodiment of the primary screen, the presence of increased alkaline phosphatase activity indicates that the substance being tested is a growth factor. Substances that are found to produce statistically significant promotion of the growth of PSC43 cells in an undifferentiated state can then be tested against normal primate-derived primordial embryonic stem cells. Substances found to be effective growth factors for these cells are then tested in combinations to determine the presence of any synergistic effects. Optionally, a secondary screen can be employed to confirm growth factors identified by the primary screen.

In one embodiment, described in detail in Section 4.4.2, the screens are performed on groups of PSC43 cells grown under four different growth conditions (alternatively, normal Rhesus, human or other primate-derived primordial stem cells can be used). A first growth condition (described in Section 4.4.2.1) includes STO (or other suitable) feeder cells in the medium described in Section 3.2.1 above. A second growth condition (Section 4.4.2.2) includes growing cells under the same conditions as the first growth condition, except that an extracellular matrix of STO or MEF cells is used in place of the feeder cells (see Section 3.2.1). A third growth condition (Section 4.4.2.3) includes growing cells on a "defined matrix" that comprises one or more substances that approximate the extracellular matrix of feeder cells. In one embodiment, the defined matrix includes one or more substances selected from the group consisting of collagen II, heparan sulfate, and merosin. Still other suitable substances can be determined using methods known in the cell culturing arts. A fourth growth condition (Section 4.4.2.4) includes growing cells under the same conditions as the first growth condition with the exception that 2.5% FBS is used in the nutrient serum instead of 20% FBS.

In one embodiment, the level of expression of alkaline phosphatase is determined for each group of cells exposed to a particular putative growth factor using the methods described herein (see Section 4.2). Substances that are correlated with increased alkaline phosphatase expression relative to unexposed control cells are considered to be growth factors. In a particular embodiment, substances found to produce an increase of alkaline phosphatase expression greater than about 20% as compared with the control are considered growth factors.

In another embodiment, substances identified as growth factors in the primary screen are tested in a secondary screen to determine the presence or absence of a correlation between exposure of the cells to the substance and a parallel increase in the expression of surface markers associated with lack of differentiation such as telomerase (described below in section 4.7), stage-specific embryonic antigen-4 (SSEA-4), stage-specific embryonic antigen-3 (SSEA-3) (both described by Kannagi et al., EMBO J, 1983, 2(12):2355-61), TRA-1-60 antigen and TRA-1-81 antigen (both described by Andrews et al., *Hybridoma*, 1984, 3(4) 347-61.

In such an embodiment, the cells are cultured as described in the primary screen. The cells are then exposed to an antibody raised against one or more of the surface marker(s) being screened, and/or the presence or absence of telomerase expression in the exposed cells is determined (see Section 4.7). In some embodiments, the surface marker antibodies are incubated with a second antibody coupled with a reporter such as a fluorescent label so that cells expressing the appropriate antigenic marker are rendered fluorescent. Labeled cells can then be sorted and counted using standard methods, e.g., a fluorescence-activated cell sorter ("FACS"). The numbers of labeled and unlabelled cells can then be compared to determine the effect of the putative growth factor. Alternatively, following exposure to unlabelled cell surface marker antibodies, the cells can be exposed to a second antibody that is specific for the cell surface marker antibody in an ELISA (Enzyme-Linked ImmunoSorbent Assay) format from which the number of cells expressing the desired surface antigen can be quantitated colorimetrically or by measurement of fluorescence. Still other methods of quantitating cells expressing surface antigens will be familiar to those having skill in the cell culture arts.

Substances identified as growth factors in the primary, and, optionally, secondary, screens are screened again using the same format as the primary screen discussed above but wherein actual primate-derived primordial stem cells are used. Those substances that are confirmed to be growth factors are then tested in combination (e.g., combinations of two or three substances) to determine the presence of any synergistic properties among the growth factors. In addition, substances that may promote differentiation or retard the growth of undifferentiated cells can be identified. For example, antibodies directed to substances in the growth medium can be added to prevent those substances from interacting with the cells being cultured.

One example of the use of the above-described techniques for determining an optimized culture medium is provided in Section 4.5 below in which alkaline phosphatase (AP) activity is used as marker for undifferentiated cells. There, PSC43 cells were grown using an STO-based extracellular matrix in a medium that included DMEM with 4.5 g/L glucose, 0.1 mM non-essential amino acids, 0.1 mM β-mercaptoethanol and 20% fetal bovine serum. To this medium sodium pyruvate, adenosine, guanosine, thymidine, cytidine, uridine, phenol red dye, and HEPES buffer were added to determine the effect of each substance individually. As described in detail in Section 4.2.1, it was determined that the addition of 1 mM sodium pyruvate to the medium resulted in an increase in the amount of AP activity. In addition a final concentration of 1 μM each of adenosine, guanosine, thymidine, cytidine and uridine to the sodium pyruvate growth medium resulted in even more enhanced AP activity levels of PSC 43 cells at both the 11$^{th}$ and 17$^{th}$ passages. The use of anti-retinoic acid antibodies to deplete the growth medium of retinoic acid also provided enhanced growth of undifferentiated cells as measured by AP activity as described in Section 4.6.

Substances identified as promoters of undifferentiated cell growth using the above-described screening methods and materials are described in Table 2 below. Those having skill in the cell culture arts will recognize that several factors identified as promoters of undifferentiated cell growth are members of the IL-6 and LIF families of cytokines. Such substances have been recognized as interacting with specific receptors that heterodimerize with gp130 to effect signal transduction (Fourcin, et al., *J. Biol. Chem.*, 271(20): 11756-11760 (1996)) and, thereby, maintenance of undifferentiated growth. Unfortunately, IL-6 and LIF-family receptors are highly species specific; therefore, growth factors isolated from one species may not function with cell lines isolated from another species. However, anti-gp130 antibodies can also be used to effect signal transduction by gp130 (Wijdenes, et al., *Eur. J. Immunol.*, 25:3474-3481). Thus, the present invention further includes methods and media for culturing primate-derived primordial stem cells including anti-gp130 antibodies.

In another embodiment, the cell culture methods and materials of the invention include a glucocorticoid, such as dexamethasone ((11β, 16α)-9-fluoro-11, 17, 21-trihydroxy-16-methylpregna-1, 4,-dien-3, 20-dione). In one embodiment, the dexamethasone is provided at a concentration of between about 1.0 nanomolar (nM) and about 10.0 μM. In one more particular embodiment, the concentration of dexamethasone is between about 1.0 nM and about 1.0 μM. In another particular embodiment, the concentration of dexamethasone is between about 1.0 nM and about 500 nM. In still another embodiment, the dexamethasone is provided at a concentration of between about 1.0 nM and about 100 nM. In yet another embodiment, the dexamethasone is provided at a concentration of about 10 nM. In still other embodiments, the dexamethasone is combined with at least one substance that is a member of the IL-1, IL-6, IL-11, or LIF families of cytokines. In some embodiments, dexamethasone is combined with at least one of the following: IL-1β (at a concentration of about 50 picograms/ml (pg/ml)), IL-6 (at a concentration of about 0.004 micrograms/ml (μg/ml)), LIF (at a concentration of about 1.2 ng/ml), and IL-11 (at a concentration of about 1.0 ng/ml).

3.4 Applications of the Cell Culture Growth Media of the Invention

The improved cell culture media and methods for growing primate-derived primordial stem cells in a substantially undifferentiated state that is provided by the present invention will be seen to be applicable to all technologies for which primate-derived cell lines are useful. Of particular importance is the use of the cell culture media and methods of culturing primate-derived primordial stem cells provided by the present invention to create new primate primordial stem cell lines having single or multiple genetic modifications which application is discussed in Section 3.4.1. Cells produced using the media and methods of the present invention can be mounted on surfaces to form biosensors for drug screening (see Section 3.4.2). In addition the observation that primate primordial stem cells are telomerase positive can be used to determine the engraftment potential of primordial stem cells, both primate-derived and non-primate-derived, as described in Section 3.4.3.

3.4.1 Creation of Primate-Derived Primordial Stem Cells Cell Lines Having Multiple Genetic Modifications In one aspect, the methods and culture media of the present invention are used to produce primate-derived primordial stem cells having single or multiple genetic modifications. Genetic alteration of cells is desirable for many reasons, such as providing modified cells for gene therapy and replacement tissues for grafting or implantation (e.g., to avoid host rejection of the cells).

According to one embodiment of this aspect of the present invention, primordial stem cells are grown using the culture media and methods described in Section 3.2.1 above. A first gene is modified in, or introduced into, at least one of the cells of the cell culture and from the resulting culture a first clone population of modified primordial stem cells is derived. The first clone population can be grown in the culture media of the invention allowing the establishment of a cell line with the desired genetic modification. If further genetic modifications are needed, a second gene is modified in, or introduced into, at least one cell of the first clone population to produce a second clone population having first and second genetic modifications. Alternatively, the first and second genetic modifications can be introduced into the same primordial stem cell with subsequent simultaneous screening for both modifications (i.e., circumventing the need to isolate a first clone population); however, the preferred procedure is a stepwise procedure.

The methods used to perform the genetic modifications to the cells can be any of those known in the molecular biological arts for making genetic transforms. Such methods include, but are not limited to, the use of positive-negative selector vectors as described in U.S. Pat. Nos. 5,464,764; 5,487,992; 5,627,059; and 5,631,153 to Capecchi, et al.; and U.S. patent application Ser. No. 081781,559. In addition, yeast artificial chromosomes (YACs) can be employed to perform genetic modifications as described in U.S. patent application Ser. Nos. 08/597,532; 08/397,547; 08/187,161; 08/276,565; 08/375,482; 08/485,505; and 08/372,482. Furthermore, isogenic DNA constructs can be used with the primordial stem cells cultured using the methods and materials provided by the present invention as described in U.S. patent application Ser. No. 08/563,138. Still other methods include those described in U.S. Pat. No. 5,591,625 to Gerson, et al. for the preparation stem cells capable of augmented expression of certain gene products, signal transduction molecules, cell surface proteins and the like for therapeutic applications. U.S. Pat. No. 5,583,016 describes methods for introducing a recombinant gene for the RNA component of telomerase into cells and GB2317891 describes methods for increasing the amount of human telomerase reverse transcriptase (hTRT) in a cell, for exampl, by introducing the reverse transcriptase subunit of telomerase into cells. These patents and patent applications are incorporated herein by reference in their entirety and for all purposes.

As is apparent to one of ordinary skill in the art, altered expression of gene products can be achieved by modifying the coding sequence of a gene product or altering flanking regions of the coding sequence. Thus, as used herein, the term "genetic modification" includes alterations to the sequence encoding a gene product, as well as alterations to flanking regions, in particular the 5' upstream region of the coding sequence (including the promoter). Similarly, the term "gene" encompasses the coding sequence and regulatory sequences that may be present flanking the coding sequence, as well as other sequences flanking the coding sequence. In addition, as is known in the art, genetic modifications can be achieved by introducing a nucleic acid that does not necessarily comprise the entire gene sequence into the cell, e.g., by introducing a nucleic acid that can be inserted into the genome by recombination.

In one embodiment of the invention in which genetically-modified primate-derived primordial stem cells are to be use for implantation into a patient, e.g., to treat Parkinson's disease, the primate-derived primordial stem cells are modified genetically to express Fas ligand (also known as CD95). Cells expressing the Fas ligand are known to induce apoptosis in T cells; thereby becoming immunologically privileged (Griffith, et al., *Science*, 270:1189-1192 (1995); Bellgrau, et al., *Nature*, 377:630-632 (1995)). In one embodiment, the present invention provides primate-derived primordial stem cells having multiple genetic modifications wherein at least one of the modifications is the expression of Fas ligand. In another embodiment, the modified primate-derived primordial stems cells are differentiated into a different cell type using, e.g., a differentiation promoter listed in Table 3 below.

3.4.2 Biosensors Comprising Primate-Derived Primordial Stem Cells

In another aspect, cells cultured and/or modified using the materials and methods provided by the present invention are mounted to support surfaces to screen for bioactive substances. In one embodiment, the cells are coupled with a substrate such that electrophysiological changes in the cells in response to external stimuli can be measured, e.g., for use as a high-throughput screen for bioactive substances. In one more particular embodiment, the cells have been transfected with DNA that targets, expresses, or knocks-out specific genes or gene products in the cell. By providing such chip-mounted cells coupled with measuring devices, such as a computer, many compounds can be screened rapidly and accurately. The biosensors could also be coupled to the measuring device in arrays for large-scale parallel screening.

In another embodiment, a reporter gene is incorporated into the DNA of a primordial stem cell that is functionally coupled with a copy of a gene associated with a particular disease state (e.g., BRCA-1 in the case of breast cancer) using the methods described in Section 3.4.1 above. In one embodiment, the reporter is sensitive to both transcription and post-transcriptional events. The primordial stem cells are allowed to differentiate such that the differentiated progeny each contain one copy of the disease gene/reporter construct. The cells are then screened against putative therapeutic agents. This allows the correlation of gene expression and responsiveness to a potential therapeutic agent with the state of differentiation of the cell. By suitable selection of the reporter, such a screening strategy can be executed with the above-described high-throughput biosensors. Still other applications of biosensors such as discussed herein will be apparent to those having skill in the art.

3.4.3 Prediction of Stem Cell Engraftment Potential of Primate-Derived Primordial Stem Cells In yet another aspect, the determination of telomerase activity as a marker for cell differentiation as described in Section 4.7 below is used to determine the engraftment potential of primate-derived primordial stem cells cultured using the methods and materials of the present invention. In one embodiment, primordial stem cells cultured using the methods and materials of the invention are allowed to differentiate, or, alternatively, induced to differentiate, to produce pluripotent daughter cells such as hematopoietic stem cells for use in transplantation. Induction of differentiation can be performed using agents effective to induce differentiation such as retinoic acid. The cells may be genetically unaltered or may be genetically modified using the methods described in Section 3.4.1 above. The pluripotent daughter cells identified as having strong telomerase expression can be specifically isolated and used for transplantation or further culturing and/or modification as described above.

In another embodiment, the use of the cell culture medium and methods of the present invention to provide cultures of unmodified and modified primate primordial stem cells is used to screen for substances that improve the monitoring of stem cells or the collection of stem cells. For example, putative engraftment enhancing substances can be added to a cell culture grown using the methods described above. Substances that increase telomerase expression compared to a control cell culture that lacks the putative enhancing substance are identified as engraftment promoters or enhancers.

4 EXAMPLES

The following Examples are provided to illustrate certain aspects of the present invention and to aid those of skill in the art in practicing the invention. These Examples are in no way to be considered to limit the scope of the invention in any manner.

4.1 Growth of Undifferentiated Primate-Derived Primordial Stem Cells

This example illustrates a method for growing primate-derived primordial stem cells on a fibroblast feeder layer with a reduced rate of differentiation.

Conditioned medium for growing ES cells was prepared using the following procedure. Mouse embryonic fibroblasts ("MEFs"), derived from dissection of 13.5-day-old embryos of CF-1 strain mice, were grown to confluence in the presence of a growth medium (hereinafter called "ES medium") prepared from 20% fetal bovine serum (HyClone), 280 osmolal Dulbecco's Modified Eagle Medium (DMEM, 4500 mg glucose per liter, with L-glutamine (GIEBCO)), 0.1 mM β-mercaptoethanol (Sigma), 0.1 mM non-essential amino acid stock (GIBCO), 1 mM sodium pyruvate (GIBCO), and a final medium concentration of 1 μM each of adenosine, guanosine, thymidine, cytidine, and uridine (Sigma). About 0.25 ml of ES medium was provided for each square centimeter of tissue culture dish surface area used for growing the MEFs (i.e., about 0.25 ml ES medium/cm$^2$). When the MEFs reached confluence, the ES medium was collected and filter-sterilized (0.2 micron filter). This medium was termed "conditioned ES medium". The conditioned ES medium was used immediately or frozen at about −80° C. until needed.

A feeder layer was prepared from irradiated MEFs by exposing MEFs suspended in a 15 ml tube containing 10 ml of ES medium to about 3,000-4,000 rads of_-radiation using a Torrex 140D model X-ray machine. After irradiation, the cells were pelleted at 1,000 rpm for 5 minutes at room temperature in a Beckman TJ-6 tabletop centrifuge. The ES medium was removed from the pelleted cells and the cells were re-suspended in fresh ES medium. The irradiated cells were then plated in gelatinized tissue culture plates at a density of approximately 5×10$^4$ cells/cm$^2$.

Rhesus monkey ES cells, isolated as described by Thomson, et al. (1995 *Proc. Natl. Acad. Sci. USA* 92:7844-7848), were plated onto the feeder layer and fresh ES medium was added to the plated cells. Colonies of undifferentiated Rhesus ES cells were detached from a feeder dish by incubating the dish with 1× 14190 D-PBS (GIBCO/BRL) containing 0.5 mM EDTA (Sigma) at room temperature for 2-5 minutes. Individual colonies of Rhesus ES cells were isolated using a small-bore pipette and transferred to an irradiated, fibroblast-coated 35 mm2 tissue culture dish containing 2.5 ml of conditioned ES medium.

The Rhesus ES colonies were gently dispersed into small clumps using a pipette (3-5 cells/clump) and transferred to a sterile 15 ml tube and pelleted at 1,000 rpm for about 5 minutes at room temperature using a Beckman TJ-6 tabletop centrifuge. The ES medium was removed, and the cells were re-suspended in 2.5 ml of fresh ES medium and transferred to a well containing a feeder layer. The ES medium was refreshed every 24 hours. The cells were passaged when the colonies became large and prior to observable indications of differentiation such as the disappearance of compact colonies of cells having a high nucleus-to-cytoplasm ratio and prominent nucleoli.

The Rhesus ES cells grown using the above-described method showed a much higher degree of undifferentiation than was observed when other procedures were used to grow such cells. A significant portion of the Rhesus ES cells remained undifferentiated as judged by both the morphology and the continued surface expression of the enzyme alkaline phosphatase (AP), as determined by the method described in Section 4.2 below. The cells were also capable of repeated passage under the same growth conditions.

4.2 Growth of Rhesus-Derived ES Cells Without a Feeder Layer

PSC43 cells were grown using the above-described conditioned medium on a fibroblast matrix that was prepared by seeding either MEFs or SIM mouse embryo-derived thioguanine- and ouabain-resistant (STO) fibroblasts (ATCC) into gelatinized tissue culture wells (1.0% weight/volume) 3-4 days prior to use. The fibroblasts (MEF or STO) were plated at a low density (approximately 1.3×10$^3$ cells/cm$^2$) and grown to confluence over three to four days. At confluence, the fibroblasts were lysed in situ. The growth medium was removed from the wells and the wells were rinsed twice with sterile 1× 14190 Dulbecco's Phosphate-Buffered Saline (D-PBS). A volume of freshly prepared lysis buffer (0.5% Triton-X100, 3.5 μl ammonium hydroxide (NH$_4$OH), and D-PBS for a total volume of 10 ml) sufficient to cover the cells of the matrix was added to the test wells. The cells were incubated with the lysis buffer at room temperature for about 10 minutes, at which time the lysis buffer was removed from the wells and the wells were rinsed three times with 1× 14040 D-PBS (Gibco-BRL; D-PBS containing 0.1 g/L anhydrous CaCl and 0.1 g/L MgCl$_2$-6H2O).

4.2.1 Supplementary Factors For Feeder-Free Growth of Rhesus-Derived ES Cells

PSC 43 cells were grown and maintained on tissue culture dishes coated with extracellular matrix made by lysing confluent primary mouse embryonic fibroblasts (MEF) as described above. The initial basic growth medium was DMEM with 4.5 g/L glucose, 0.1 mM non-essential amino acids, 0.1 mM β-mercaptoethanol and 20% fetal bovine serum. The above-described basic growth medium was supplemented with the following substances: sodium pyruvate, adenosine, guanosine, thymidine, cytidine, uridine, phenol red dye, and HEPES buffer. The cells were cultured in the media so supplemented at media volumes corresponding to approximately one-half the total cell surface area with re-feedings every 24-48 hours, for 7 days. AP activity was then measured as described in Section 4.3.

The addition of 1 mM sodium pyruvate to the medium resulted in an increase in the amount of AP activity. The further addition of a final concentration of 1 μM each of adenosine, guanosine, thymidine, cytidine and uridine to the sodium pyruvate growth medium resulted in even more enhanced AP activity levels of PSC 43-cells at both 11 and 17 passage numbers. Removal of phenol dye or the addition of HEPES buffer had no effect on AP measurements.

The use of media having reduced endotoxin levels (about 0.03 endotoxin units/ml) also showed beneficial properties. Furthermore, the use of DMEM having a reduced osmolarity of 280 mOsm/kg also provided enhanced growth conditions. R366.4 Rhesus embryonic stem cells (Thomson and Marshall, "Primate Embryonic Stem Cells"; *Current Topics in Developmental Biology* 38:133-164) grown in a 280 mOsm/kg medium showed enhanced AP activity compared to cells of the same lineage grown in typical medium having a osmolarity of 330-340 mOsm/kg. In addition, optimal cell density for plating the PSC 43 cells was determined to be 1.3-2.2×10$^4$ cell/cm$^2$.

4.3 Quantitation of Undifferentiated Primate-Derived Primordial Stem Cell Propagation This example illustrates a method for quantitating the proliferation of undifferentiated primordial stem cells by measuring the degree of alkaline phosphatase ("AP") activity of such cells.

Rhesus or PSC43 cells were grown using the methods described in Sections 4.1 and 4.2. The medium was removed from the cells by aspiration and the cells were washed with 1 ml of phosphate-buffered saline ("PBS"). About 1 ml of the AP substrate, 4-methylumbelliferyl phosphate ("4-MUP"), at a concentration of about 0.2 mM in serum-free DMEM medium was added to the cells. The cells were incubated at 37° C. for between about 1 hour and about 2 hours at which time the amount of fluorescent product was measured using a CYTOFLUOR II plate reader at an excitation wavelength of 360 nm and an emission wavelength of 448 nm.

4.4 Screen for Factors that Enhance Proliferation of Undifferentiated PSCs

This example describes a screen for identifying factors that enhance the proliferation of primnate-derived primordial stem cells in an undifferentiated state using the cell growth conditions and alkaline phosphatase activity measurements described above.

4.4.1 Overview

PSC 43 cells were grown under four different conditions as described in Section 4.4.2 below. Cells grown under each of the four conditions were plated in six wells of a 24-well microtiter plate. The four plated sets of cells were then exposed to one or more putative growth factors and the effects of those putative factors on the growth of cells in an undifferentiated state was determined by measuring AP activity as described in Section 4.2 above in a primary screen which is described in Section 4.4.3. Substances showing effectiveness in the primary screen were then subjected to a confirmation screen in which the putative growth factor was tested against primate-derived primordial stem cells as described in Section 4.4.4. Finally, growth factors showing effectiveness in both screens were examined in duplicate and triplicate combinations to investigate possible synergies among the factors as described in Section 5.4.5.

Growth conditions 1 and 2 described in Sections 4.4.2.1 and 4.4.2.2 below were used to examine the effects of putative growth factors on the proliferation of PSC43 cells in an undifferentiated state grown with and without a feeder later. Growth condition 3 described in Section 4.4.2.3 below used a reduced serum concentration (2.5%) to slow down the growth of cells in view of the observation that PSC43 cells have extremely fast population doubling time of 14-15 hours in growth medium containing 20% serum. Growth condition 4 described in Section 4.4.2.4 below was designed to examine the effect of extracellular matrix (ECM) components on the response of PSC43 cells to a putative growth factor, e.g., to determine whether the ECM components sequester, block, or enhance thie action of a putative growth factor.

4.4.2 Growth Conditions

4.4.2.1 Growth Condition 1

One set of PSC 43 cells was grown using the method described in Section 4.1 above using irradiated MEF cells that were prepared as follows. MEF cells were grown in a medium ("MEF medium") that included DMEM medium containing 10% fetal bovine serum ("FBS") without antibiotics. Standard 24-well tissue culture plates were coated with 0.5% gelatin overnight at 37° C. The following day the cells were trypsinized, counted, and irradiated at 4,000 rads. The gelatin was removed from the plates, and the irradiated cells were plated at a density of 100,000 cells/well as a feeder layer. The cells were allowed to attached to the wells overnight and about 25,000 PSC 43 cells per well were then plated over the cells.

4.4.2.2 Growth Condition 2

A second set of PSC 43 cells was grown using the method described in Section 4.1 on an extracellular matrix of STO or MEF cells. STO or MEF extracellular matrix was prepared as follows. Stock cultures of STO or MEF cells were grown in their respective media. Standard 24-well tissue culture plates were coated with 0.5% gelatin overnight at 37° C. after which time the gelatin was removed from the wells. The STO or MEF cells were trypsinized, counted, and plated in the wells at a density of about 50,000 cells/well and allowed to grow to confluence. The cells were then washed once with 1 ml of PBS and lysed for a minimum of 10 minutes with 0.5 ml of the above-described lysis buffer. The lysis buffer was removed, and the wells were washed three times with 1 ml of PBS containing calcium and magnesium. About 0.5 ml of ES medium was then added to each well, and the plates were stored at 37° C. until plated with PSC 43 cells as described above.

4.4.2.3 Growth Condition 3

A third set of PSC 43 cells was grown as described in Section 4.1 on the above-described STO extracellular matrix using, however, 2.5% fetal bovine serum in place of the 20% FBS described. Twenty-four hours after plating of the cells, the medium was removed and fresh medium containing the putative growth factor was added.

4.4.2.4 Growth Condition 4

A fourth set of PSC 43 cells was grown using several different substances to determine an extracellular matrix (ECM) capable of supporting the proliferation of primate-derived primordial stem cells.

4.4.3 Primary Screen

Putative growth factor-containing medium was prepared as follows. Fifteen milliliters of ES medium were aliquoted into a 15 ml conical tube. An aliquot of a stock solution containing the putative growth factor was added and the combined solution was sterilized by filtration through a 0.2 μm Acrodisc filter coupled with a 20 ml syringe. The final concentration of the growth factor solution was five-times the published median effective dose ($ED_{50}$), i.e., the dose that produces an observable result in 50% of the treated cell population, for the putative growth factor being tested. A summary of published ED50 values can be found in the 1997 Cytokine Source Book from R&D Systems, Inc., Minneapolis, Minn.

The ES medium from each of the 24 wells of the plate being tested was removed by aspiration, and 1.5 ml of the above-described putative growth factor-containing medium was added, in triplicate, to the wells. Six wells were filled with a control solution made from ES medium containing PBS and 0.1% BSA. The control wells were chosen randomly on the plate to reduce the possibility of systematic errors. The PSC 43 cells were allowed to incubate with the putative growth factor-containing medium for four days. The putative growth factor-containing medium was removed and replaced with fresh putative growth factor-containing medium at the second or third day.

On the fourth day, the cells were assayed for alkaline phosphatase activity as described in Section 4.3. Substances differing from the control by more or less than 20% of the control value were considered to promote the growth of undifferentiated PSC43 cells. A substance that increased the amount of alkaline phosphatase activity by more than 20% were in a substantially undifferentiated state.

Substances that showed activity as growth factors were examined in the secondary screen described below. Those substances that demonstrated strong differentiation promotion or suppression properties in both screens were examined using the tertiary screen directly.

Over 200 potential growth substances belonging to the EGF, FGF, Interleukin, TNF, LIF, GRO, NGF, Insulin-like, PDGF, the C-C Chemokine families, as well as growth-factor-neutralizing antibodies, were screened using the above-described protocol. In addition, the substances angiogenin, anti-angiogenin, PD-ECGF, anti-PD-ECGF, TPO, anti-TPO, HGF, anti-HGF, CTLA-4/F, chimera, HCC-1, I-309, IP-10, MIG, SLPI, anti-SLPI, Strom CDF-1β, EPO, EPO soluble receptor, anti-EPO, Flt-1/$F_c$chimera80, Flt-3 ligand, anti-Flt-3 ligand, GCSF, anti-GCSF, GMCSF, anti-GMCSF, IFN-γ, anti-IFN-γ, leptin, MCSF, anti-MCSF, SCF, anti-SCF, ENA-78, and anti-ENA-78 were also screened. Substances that increased the amount of AP activity by more than 20% as compared to the control were classified as promoters of undifferentiated cell growth. These substances are shown below in Table 2, which lists the promoter and the effect of the promoter on the growth of undifferentiated cells as a percentage of the control. Substances that decreased the amount of AP activity by more than 20% were classified as differentiation promoters and are listed below in Table 3, which lists the differentiation promoter and the effect of the differentiation promoter on the growth of undifferentiated cells as a percentage of the control. The concentrations screened are in parentheses.

TABLE 2

| | |
|---|---|
| Anti-TGF-β3 (0.6 µg/ml) | Anti-PDGFbb (2.0 µg/ml) |
| CNTF (15.0 ng/ml) + Soluble CNTF Receptor (2.0 µg/ml) | Anti-TGF-β5 (100.0 ng/ml) |
| Anti-VEGF (0.16 µg/ml) | Anti-TGF-β (20.0 µg/ml) |
| MCP-1 (100.0 ng/ml) | IL-17 (30.0 ng/ml) |
| IL-1α (35.0 pg/ml) | IL-1β (50.0 pg/ml) |
| Flt-3 Ligand (2.0 ng/ml) | Anti-IL-8 (20.0 µg/ml) |
| Anti-BDNF (30.0 µg/ml) | Anti-TNF-β (400.0 ng/ml) |
| IL-11 (1.2 ng/ml) | IL-6 (4.0 ng/ml) |
| LIF (1.0 ng/ml) | Anti-HB-EGF (12.0 µg/ml) |
| IL-6 (4.0 ng/ml) + Soluble IL-6 Receptor (45.0 ng/ml) | TGF-β LAP (200.0 ng/ml) |
| BFGF (1.25 ng/ml) | FGF-4 (750.0 pg/ml) |
| PDGF Soluble Receptor A (15.0 µg/ml) | Forskolin (10.0 µg/ml) |
| Dexamethasone | |

TABLE 3

| | |
|---|---|
| PDGF (15.0 ng/ml) | PDGFaa (25 ng/ml) |
| PDGFab (15.0 ng/ml) | PDGFbb (15.0 ng/ml) |
| HB-EGF (25.0 ng/ml) | TGF-α (2.0 ng/ml) |
| TGF-β1 (300.0 pg/ml) | EGF (2.0 ng/ml) |
| Betacellulin (1.5 ng/ml) | TGF-α1.2 (400.0 pg/ml) |
| TNF-β (250.0 pg/ml) | TNF-α (250.0 pg/ml) |
| TGF-β2 (1.0 ng/ml) | TGF-β3 (150.0 pg/ml) |
| Anti-CNTF (120.0 µg/ml) | RANTES (1.0 µg/ml) |

4.4.4 Confirmation Screen

Factors that demonstrated effect in the primary and secondary screens were screened in a tertiary screen using Rhesus ES cells to confirm the results of the earlier screens.

Rhesus ES cells were grown as follows. Eight to ten colonies of the cells were picked, dissociated, pelleted, and resuspended in about 24 ml of ES medium. About 1 ml of the cell suspension was added to each well of a feeder-coated 24-well plate. The plated cells were left overnight.

About 1.5 ml of growth factor- or control-containing ES medium, prepared as described above, was added to each of the wells. The cells were left to grow for six days in the presence of the growth factor(s) during which time the medium was replaced on days two and four. The cells were then allowed to grow for two more days at which time they were tested for AP activity. The number and size of the Rhesus cell colonies was noted and compared with the number and size of the control colonies. If the numbers and sizes of the control colonies were consistent with the degree of AP activity observed, then the results of the confirmation screen were considered consistent with the results of the primary screen.

4.4.5 Screen for Synergistic Effects

Growth factors that demonstrated effects in all assays are included in duplex and triplex screens to determine the presence of any synergistic effects among the growth factors. These screens are run as described above with the exception that two- and three-way combinations of those growth substances identified by at least the primary and confirmation screens as active are used in place of individual growth factors. Combinations that provide superior qualities as compared the qualities of the individual components will be included as media supplements.

4.5 Screen for Extracellular Matrix Components for Feeder-Free Growth of Primate-Derived Primordial Stem Cells The above-described PSC 43 cells were grown on a defined matrix of selected extracellular materials. The PSC 43 cells were plated in the wells of 24-well plates that had been coated with one of the following substances: collagen II, collagen III, collagen IV, collagen V, prepared extracellular matrix (partially purified matrix extract of human placenta, available commercially from SIGMA), fibronectin, laminin, merosin (laminin homolog), tenascin, heparan sulfate, chondroitin sulfate, dermatan sulfate, aggrecan, biglycan, thrombospondin, vitronectin, or decorin. Cells were also plated in wells that had been coated with one of the listed substance and gelatin, alone or in combination with fibronectin. Cells were grown for about 6 days at which time the growth of cells remaining in an undifferentiated state was measured. The growth of PSC43 cells in an undifferentiated state using these substances and combinations was measured by determining the expression of alkaline phosphatase as described in Section 4.2 above and compared to the growth of PSC43 cells in control wells on STO cells.

The results of the screen are provided in Table 4 below. Substances and/or combinations that provided an increase in AP activity of greater than about 20% as compared to the control were determined to be positive factors for feeder-free growth of primate-derived primordial stem cells. As seen from the data in Table 4, merosin, merosin combined with gelatin, and all combinations of collagen II and heparan sulfate were found to be positive factors for feeder-free growth of primate-derived primordial stem cells. The concentration of the putative matrix component being screened is provided in parentheses.

TABLE 4

| Putative Matrix Component | Growth of Undifferentiated PSC 43 Cells as a Percentage of Control |
|---|---|
| Merosin (10.0 µg/cm$^2$) | 233 |
| Collagen II (10.0 µg/cm$^2$) | 227 |
| Heparan Sulfate (3.0 µg/cm$^2$) | 206 |
| Gelatin (0.5%) | 180 |
| Fibronectin (5.0 µg/cm$^2$) | 146 |
| Tenasin (10.0 µg/cm$^2$) | 128 |
| Dermatan Sulfate (3.0 µg/cm$^2$) | 128 |
| Collagen IV (1.0 µg/cm$^2$) | 126 |
| Collagen III (1.0 µg/cm$^2$) | 126 |
| Vitronectin (50.0 ng/cm$^2$) | 126 |
| Decorin (10.0 µg/cm$^2$) | 125 |

4.6 Growth Conditions for Enhancing the Maintenance of Undifferentiated PSCs

The Example demonstrates the addition of anti-retinoic antibodies in the growth medium of primate-derived primordial stem cells to enhance growth of such cells in an undifferentiated state.

PSC43 cells (at passage number 17, post-feeder) were plated onto dishes coated with a fibroblast matrix prepared from lysed fibroblasts and conditioned medium as described above. The cells were maintained using a growth medium containing DMEM with 4.5 g/L glucose, 0.1 mM non-essential amino acids, 0.1 mM β-mercaptoethanol and 20% fetal bovine serum which had been conditioned as described above. This medium was supplemented with anti-retinoic acid antibodies at final concentrations of either 1 µg/ml or 10 µg/ml. The antibodies had been prepared as described in Zhoe et al., 1991 *J. Nutr. Biochem.* 2:122-131 and Zhoe et al., 1991 *J. Immunol. Methods* 138:211-223. A control was also prepared in which PSC 43 cells were grown in the same medium as just described but without anti-retinoic acid antibodies.

The AP levels of the cells were measured as described above after one week in culture. A 27% increase in AP activity was observed in those cultures that had been supplemented with anti-retinoic acid antibodies. Addition of anti-retinoic acid antibodies at either 1 µg/ml or 10 µg/ml provided the same effect. These results indicate that conditioned ES medium including anti-retinoic acid antibodies enhances the growth of undifferentiated primate-derived primordial stem cells.

4.7 Determination of Telomerase Activity in Primate-Derived PSCs

This Example illustrates the detection of telomerase activity in primate-derived primordial stem cells as a marker for undifferentiation in such cells.

Cell extracts of undifferentiated rhesus monkey primordial stem cells, differentiated Rhesus monkey primordial stem cells, mouse embryonic fibroblast cells, and 293 cells were prepared by a modification of the detergent lysis method described by Kim, et al., (*Science* 266:2011 1994) in which the cells were washed with phosphate buffered saline and lysed with CHAPS lysis buffer for 30 minute on ice. The MEF, differentiated cell, and undifferentiated ES cell extracts were prepared at concentrations of 10,000 cells/µl of CHAPS lysis buffer, 20,000 cells/µl of CHAPS lysis buffer, and approximately 1,000 cells/µl of CHAPS lysis buffer, respectively. The control, telomerase-positive 293 cell extract (an adenovirus-transformed human kidney cell line) was prepared at 1,000 cells/ml in CHAPS lysis buffer. The lysed cells were centrifuged at 12,000 g for 30 minutes at 4° C. and the cell extracts (the supernatants) were removed.

Telomerase activity in the cell extracts was determined using a modified PCR-based TRAP assay. A modified reverse primer (RP, 5'-GCGCGG(CTTACC)$_3$CTAACC-3', SEQ. ID. NO:1) and a $^{32}$end-labeled forward primer (TS, 5'-AATC-CGTCGAGCAGAGTT-3', SEQ. ID. NO:2) were synthesized using standard methods and materials. Two µL of each cell extract were combined with 48 µL of a mixture containing 20 mM Tris-HCl pH 8.3), 1.5 mM MgCl$_2$, 63 mM KCl, 0.05% Tween™20, 1 mM EGTA, 0.1 mg/mL bovine serum albumin (BSA, fraction V, purchased from Boehringer Mannheim), 2 µg/mL TS. 2 mg/mL RP, 50 µM each of dATP, dCTP, dTTP, dGTP and 0.04 Units/µL Taq polymerase. PCR amplification was performed for 27 cycles, each cycle being a sequence of amplification at a temperature of 94° C. for 30 seconds, 60° C. for 30 seconds, and 72° C. for 30 seconds. Following PCR, the samples were resolved by polyacrylamide gel electrophoresis on a 15% non-denaturing polyacrylamide gel. The gels were dried and the products visualized using a phosphorimager. A control sample containing 0.2 units of RNAse for each cell extract was also prepared and analyzed. Quantitation of the PCR products was conducted by comparing signals from serial dilutions of cell extracts to those from serial dilutions of telomerase-expressing 293 cells. The cell extracts had been normalized for protein concentration. Protein determination was done using the Coomassie Protein Assay Reagent (Pierce #23200) using BSA as standard.

Undifferentiated Rhesus monkey ES cells showed high levels of telomerase activity, whereas feeder and differentiated rhesus monkey cells had no detectable telomerase activity. The undifferentiated Rhesus monkey ES cells also demonstrated greater than 2.5-fold level of telomerase activity compared with 293 cells. A comparable level of cell extract from MEF cells showed very faint or no detectable telomerase signals. The latter result also demonstrated that the observed telomerase signal in the undifferentiated Rhesus primordial stem cells did not arise from contamination of the sample of undifferentiated Rhesus cells by MEF cells.

5 CONCLUSION

Thus, the present invention provides novel materials and methods for growing primate-derived primordial stem cells in a substantially undifferentiated state. Using the methods and materials provided the present invention primate-derived primordial stem cells, such as primordial stem cells isolated from humans and monkeys, can be grown more efficiently. The ability to grow efficiently such cells without differentiation has important applications for therapeutic uses of primordial stem cells for treating human diseases using tissue transplantation and/or gene therapy techniques where such cells are used directly or following one or more genetic modifications as described herein. In addition, primate-derived primordial stem cells grown using the methods and materials described herein can be used to screen for new bioactive substances or for other factors that promote or retard the differentiation of such cells in culture.

What is claimed:

1. A method of culturing primate primordial stem (pPS) cells to proliferate in an undifferentiated state, comprising contacting the primate primordial stem cells with an extracellular matrix and a cell culture medium in a growth environment free of feeder cells, wherein the extracellular matrix is a fibroblast matrix, prepared by culturing fibroblasts, lysing the fibroblasts in situ, and then washing what remains after lysis.

2. A method of culturing primate primordial stem (pPS) cells to proliferate in an undifferentiated state, comprising contacting the primate primordial stem cells with an extracellular matrix and a cell culture medium in a growth environment free of feeder cells, wherein the nutrient medium comprises sodium pyruvate and nucleosides, and has a low endotoxin level.

3. A method of culturing primate primordial stem (pPS) cells to proliferate in an undifferentiated state, comprising contacting the primate primordial stem cells with an extracellular matrix and a cell culture medium in a growth environment free of feeder cells, wherein the nutrient medium contains added fibroblast growth factor.

4. A method of culturing primate primordial stem (pPS) cells to proliferate in an undifferentiated state, comprising contacting the primate primordial stem cells with an extracellular matrix and a cell culture medium in a growth environment free of feeder cells, wherein the nutrient medium contains added forskolin.

5. A method of culturing primate primordial stem (pPS) cells to proliferate in an undifferentiated state, comprising contacting the primate primordial stem cells with an extracellular matrix and a cell culture medium in a growth environment free of feeder cells, and further comprising testing the pPS cells for expression of telomerase.

* * * * *